United States Patent
Fischer

(10) Patent No.: US 10,528,990 B2
(45) Date of Patent: Jan. 7, 2020

(54) METHOD OF RAISING FUNDS FOR AN ORGANIZATION

(71) Applicant: John G. Fischer, Irving, TX (US)

(72) Inventor: John G. Fischer, Irving, TX (US)

(73) Assignee: Tooth Fairy Designs, Inc., Irving, TX (US)

( * ) Notice: Subject to any disclaimer, the term of this patent is extended or adjusted under 35 U.S.C. 154(b) by 169 days.

(21) Appl. No.: 15/403,081

(22) Filed: Jan. 10, 2017

(65) Prior Publication Data

US 2017/0148069 A1    May 25, 2017

Related U.S. Application Data

(63) Continuation of application No. 13/842,556, filed on Mar. 15, 2013, now Pat. No. 9,542,702, which is a continuation-in-part of application No. 13/557,016, filed on Jul. 24, 2012, now Pat. No. 8,661,849, which is a continuation-in-part of application No. 12/699,476, filed on Feb. 3, 2010, now Pat. No. 8,226,877.

(51) Int. Cl.
| | |
|---|---|
| *G06Q 30/02* | (2012.01) |
| *G06Q 30/06* | (2012.01) |
| *A44C 27/00* | (2006.01) |
| *A61C 19/00* | (2006.01) |

(52) U.S. Cl.
CPC ......... *G06Q 30/0279* (2013.01); *A44C 27/00* (2013.01); *A61C 19/008* (2013.01); *G06Q 30/0269* (2013.01); *G06Q 30/0601* (2013.01); *G06Q 30/0621* (2013.01); *G06Q 30/0635* (2013.01)

(58) Field of Classification Search
None
See application file for complete search history.

(56) References Cited

U.S. PATENT DOCUMENTS

| | | | |
|---|---|---|---|
| 5,755,116 A | 5/1998 | Sparacino et al. | |
| 5,762,502 A | 6/1998 | Bahn et al. | |

(Continued)

FOREIGN PATENT DOCUMENTS

| | | |
|---|---|---|
| JP | 2002-219009 A | 8/2002 |
| JP | 2006-255367 A | 9/2006 |
| TW | 2008-819092 A | 5/2008 |

OTHER PUBLICATIONS

Human Teeth Jewelry, http://www.stylelist.com/2007/05/22/human-teeth-jewelry/, published Aug. 22, 2007.

*Primary Examiner* — Julie M Shanker

(57) ABSTRACT

The present invention relates to a method of raising funds for an organization. In one embodiment, the organization distributes a solicitation to a buyer, or for delivery to a buyer by way of a child relative of the buyer. The solicitation comprises an offer to sell a jewelry article made from a processed exfoliated deciduous tooth of the child, set in a jewelry object, as a gemstone would be set. The buyer sends a payment for the jewelry article to the manufacturer, who sends a payment to the organization for having distributed a solicitation that was converted into a purchase. The buyer sends the exfoliated deciduous tooth to the manufacturer. The deciduous tooth is specially processed in a manner that allows it to be set in the buyer's selected jewelry object as a gemstone would be set to create the completed jewelry article.

25 Claims, 13 Drawing Sheets

(56) References Cited

U.S. PATENT DOCUMENTS

| | | |
|---|---|---|
| 6,200,507 B1 | 3/2001 | Dennis |
| 7,228,602 B2 | 6/2007 | Weisbrot et al. |
| 8,226,877 B2 | 7/2012 | Fischer |
| 8,661,849 B2 | 3/2014 | Fischer |
| 9,542,702 B2 | 1/2017 | Fischer |
| 2002/0025392 A1 | 2/2002 | Yardley et al. |
| 2003/0194678 A1 | 10/2003 | Viltro et al. |
| 2008/0053149 A1 | 3/2008 | Benos |

| Tooth Eruption Chart | | |
|---|---|---|
| Tooth | Primary | Permanent |
| Upper Teeth | | |
| Central Incisor | 8-12 months | 7-8 years |
| Lateral Incisor | 9-13 months | 8-9 years |
| Canine | 16-22 months | 11-12 years |
| 1st Premolar | | 10-11 years |
| 2nd Premolar | | 10-12 years |
| 1st Molar | 13-19 months | 6-7 years |
| 2nd Molar | 25-33 months | 12-13 years |
| Wisdom Tooth | | 17-21 years |
| Lower Teeth | | |
| Central Incisor | 6-10 months | 6-7 years |
| Lateral Incisor | 10-16 months | 7-8 years |
| Canine | 17-23 months | 9-10 years |
| 1st Premolar | | 10-12 years |
| 2nd Premolar | | 11-12 years |
| 1st Molar | 14-18 months | 6-7 years |
| 2nd Molar | 23-31 months | 11-13 years |
| Wisdom Tooth | | 17-21 years |

*FIG. 4*

METHOD OF RAISING FUNDS FOR AN ORGANIZATION

CROSS-REFERENCES TO RELATED APPLICATIONS

This application is a continuation of U.S. application Ser. No. 13/842,556, now U.S. Pat. No. 9,542,702, which is a continuation-in-part of U.S. application Ser. No. 13/557,016, now U.S. Pat. No. 8,661,849, which is a continuation-in-part of U.S. application Ser. No. 12/699,476 filed on Feb. 3, 2010, now U.S. Pat. No. 8,226,877.

BACKGROUND OF THE INVENTION

The present invention relates to jewelry (including keepsake items), and more particularly to such items made of human bone. One embodiment discloses jewelry made of pulverized and recombined primary human teeth, or baby teeth. The baby tooth is partially or fully pulverized and bonded with a chemical bonding agent in a mold or pre-formed frame to create designs personalized to the family members. In another embodiment, the hollow interior crown of the deciduous tooth is filled with a solidifying bonding agent, and the tooth shaped to form a solid "tooth stone" that can be mounted in a metal jewelry object as a gemstone would normally be mounted.

More particularly, the present invention relates to a method of marketing the Deciduous Teeth Matrix Jewelry in a way that can be used to raise funds for charitable organizations and other groups. The novelty of the manufacturing process for the product and required exchange of the biological materials raises new marketing obstacles and constraints which the present invention advantageously solves.

One embodiment discloses jewelry made of pulverized and recombined primary human teeth, or baby teeth. When a parent saves the baby teeth of his/her children, the teeth would be partially or fully pulverized and bonded with a chemical bonding agent in a mold or pre-formed frame to create designs personalized to the family members. In another embodiment disclosed herein, processing improvements are disclosed, including an embodiment in which the hollow interior crown of the deciduous teeth is filled with a solidifying bonding agent, and the tooth shaped to form a solid "tooth matrix" that can be mounted in a metal jewelry article as a gemstone would normally be mounted.

Particular to the present invention, an embodiment is disclosed for a method of raising funds for an organization, in which the products and processes disclosed in the above identified related patent and application are used to provide a new method of raising funds for an organization.

Jewelry made from the bones and teeth of animals has been known and made and worn in early civilizations. From shark teeth to bear claws, man has adorned his body with animal tissue for both necessity and vanity since before written history. Even today, shark teeth are a popular necklace. It is believed the Vikings may have made jewelry from human teeth. It has also been known to string teeth together for attachment to a necklace. It has also been known in Costa Rica and Chile to set the solid deciduous dentition pieces in gold or silver, to make a necklace or earring.

What has not known to have been done is to manufacture jewelry from processed human deciduous dentition, as in the manner disclosed. The hardest thing in the human body is the enamel on the teeth. Like all mammals, humans have primary teeth and permanent teeth. Teeth begin being formed before birth.

Human teeth are very hard in order to withstand the grinding forces associated with chewing and crunching food. The hard material of the tooth is composed of calcium, phosphorus and other mineral salts. The material in the majority of the tooth is called dentine. The hard, shiny exterior layer is the enamel.

Teeth have two basic parts; a root to anchor the tooth to the jaw and a crown above the gum line. The section where the crown meets the root is called the neck. The root is covered with a hard material called cementum. At the center of each tooth is an area with nerves, arteries and veins called the dental pulp.

Humans have four different types of teeth, each with a different function: Incisors for cutting off bites of food; cuspids (with long sharp points) for tearing food; bicuspids (with two points) to tear and crush food; and molars with large, relatively flat surfaces to crush and grind food.

The four types of teeth together allow humans to be omnivores (eating both meat and vegetables). Most animals have more specialized teeth. Carnivorous (meat eating) animals have long sharp tearing teeth. Grazing animals, like cows and horses, have large flat teeth for grinding grass and other vegetation. Deciduous dentition is also known as the primary, baby, milk, or lacteal dentition.

The term deciduous means "to fall off." Although deciduous teeth are in time replaced by the succedaneous, or permanent, teeth, they are very important to the proper alignment, spacing and occlusion of the permanent teeth. The deciduous incisor teeth are functional in the mouth for approximately five years, while the deciduous molars are functional for approximately nine years. They therefore have considerable functional significance. The progressive loss of deciduous teeth are considered an important milestone in the developmental phase of childhood.

The events are often marked by celebration, traditions and superstitions around the world. In the United States, tradition is based on tales of the Tooth Fairy. In Australia, mothers are once believed to have crushed their children's baby teeth and eaten the powder.

In some parts of the world, a child's baby tooth was placed in nests where rats or snakes were known to live because people believed evil witches disliked those animals and wouldn't go near them. In many parts of the world, parents placed their children's teeth in mouse nests. They thought that would result in a new tooth growing in the lost tooth's place, just as a mouse's lost teeth somehow re-grew.

In other parts of the world, mothers hid their children's teeth from animals because they believed if an animal found the tooth, a tooth like that animal's would grow in the mouth of the child. In parts of England, mothers at one time burned their children's baby teeth so that evil witches couldn't get their hands on them and gain control of the children.

In the United States and elsewhere, it is common for parents to save, at least for a while, the exfoliated baby teeth of their children as a keepsake of their childhood and development. The typical storage means is a small envelope, or decorative box. One disadvantage of this method of saving deciduous teeth is that the deciduous teeth are biologically contaminated. Another disadvantage of this method is that a small box filled with tiny teeth isn't significant as a keepsake, other than the origin of the teeth themselves.

Another disadvantage of storing deciduous teeth is that the collective individual teeth are easily lost or mixed up with the teeth of other children. Another disadvantage of storing deciduous teeth is their natural geometry combined with bloodstains lacks the display appeal of photographs, gifts, letters, and other memorabilia.

Deciduous teeth are also very different from adult teeth in size, shape, number, and hardness. Each of these differences render the deciduous teeth far more difficult to work with in comparison to gem stones or adult teeth. In particular deciduous teeth cannot be readily shaped or mounted in their native state without crumbling.

A primary problem is that the deciduous teeth are contaminated with bloodstains and residual pulp that are difficult to remove. A significant difficulty in the process of shaping exfoliated deciduous teeth into jewelry is that they have resorbed roots, leaving only a thin crown with a hollow interior space. This renders the deciduous teeth extremely brittle and not shapable with standard lapidary and machining techniques. Further, machining or hand shaping to a depth past the exterior wall exposes the hollow interior, thereby ruining the aesthetic appearance of the article.

Another difficulty in modifying exfoliated deciduous teeth into jewelry or keepsakes is that the disinfecting process can make the teeth even more brittle, and subject to fracture.

Another difficulty in modifying exfoliated deciduous teeth into jewelry or keepsakes is that they often contain thin fractures that cause the teeth to fracture when handled, and may break if dropped even a few inches onto a hard surface. Besides tending to cause the teeth to fracture when handled, the fracture lines will absorb the dye from a conventional lapidary doping wax used to hold the tiny teeth, ruining the appearance of the specimen.

Another difficulty in modifying exfoliated deciduous teeth into jewelry is their very small size, which makes them extremely difficult to handle for cleaning or machining.

Another difficulty in modifying exfoliated deciduous teeth into jewelry is that the dentition varies significantly with gender, race, nutrition, and other factors, such that individual dentition will have varying machinability properties.

Regarding the present invention, it is known to raise funds for organizations by having the organization send solicitations that are directed to a parent or other adult caretaker of a child (buyer). The best known of these is for school pictures. The organization may provide a printed solicitation to children to deliver to the buyer. The buyer chooses a picture or group of pictures they would like, and marks the selection on the solicitation and returns it with a check or other authorization for purchase. The photography company then takes pictures of the children at the school and provides the photographs to the buyers as ordered. The school will then receive a percentage of the sale made to the buyer. Similar events are conducted for sports teams for children participating in sports.

There are several disadvantages to this method. A first disadvantage is that the process is as old as rocks, and thus provides little excitement among buyers. Another disadvantage is that the vast majority of parents and caretakers now have their own digital camera, including in their phone, making it harder for parents to justify buying them when they can take as many as they want for free. Another disadvantage is that many parents and caretakers also have photograph manipulation software, such as Photoshop®, allowing them to create more special effects for free than the photographer can even offer. Another disadvantage is that kids get sick, and might miss photo-day, which is not a problem when taking them at home. Another disadvantage is that sometimes kids cry, or make a funny face or just frown. A great many parents know what this can be like. Once again, at home, the parent or caretaker can just keep snapping more pictures and keep the several that they like best.

Another disadvantage, is that while a professional photographer will be assigned to take the photographs, that requires a commitment of collective travel and time at the location on the scheduled day. With the price pressure created by the proliferation of home digital cameras, this method of raising funds relies heavily on volume for effectiveness. This renders this option impractical for small organizations.

Other well-known methods of raising funds for organizations that involves children include candy sales, car washes, and cookie sales. A primary disadvantage of this method is that, while picture day at school might involve wearing an undesirable outfit or an unwanted haircut, these other methods are distinguished in that they require at least some element of child labor. Another disadvantage is that many kids just don't want to do this. Another disadvantage is that they also require the interaction of the children with "stranger dangers" who are the prospective buyers. Allowing the children to walk unescorted door-to-door has become completely unacceptable for most parents.

As a result, another disadvantage is that the parent or other adult caretaker has to be unwillingly involved. This can mean hours of time in bad weather in an undesirable neighborhood. Another disadvantage is the alternative of setting up a small table in front of a store and making the customers feel uncomfortable when walking past the small child in the cute uniform, again, under parental supervision. Another disadvantage is the option of the parent buying up far more than a desired share of the cookies themselves, and filling the shelves at home in hopes that the family members will eat them over the following several months before they go stale. Since these are not granola bars, eating a great many of them is not healthy.

Another disadvantage is that in desperation of avoiding the other alternatives, parents and caretakers offer them to co-workers, where they will be obligated to buy them from all of the other co-workers if they have a shred of decency. Still, this is often preferable to spending hours trying to supervise the sale of as many cookie boxes as possible, with the slim hope that the excited child will be rewarded with a cheap token of appreciation from the organization. Another disadvantage is that margins per box are relatively small, requiring high volumes of sales to raise sufficient funds.

The present invention provides a method that overcomes the disadvantages of the other traditional methods outlined above. First, despite centuries of fund raising activities, it offers a method and product that is entirely new, and never before offered for this purpose, thus generating interest associated with its novelty. Second, it is associated with a physical milestone in life, which other fund raising opportunities do not do. Third, it provides a means of making a beautiful article out of something that a great many parents are already saving, in a rather unsightly and unusable form. Fourth, it does not require preparation or attendance of the child. Fifth, it does not involve any child labor. Sixth, it does not require any parental participation. Seventh, it provides a jewelry buying opportunity for parents. Eighth, it provides a significantly larger margin per sale than does photography or cookie and candy sales. Ninth, it does not rely on volume sales, so it is a viable option for small organizations. Tenth, it does not compete with, nor interfere with, traditional, respected methods of fund raising, allowing organizations to continue those methods, while adding a new and interesting fund raising resource.

Other advantages of the present invention will become apparent from the following descriptions, taken in connection with the accompanying drawings, wherein, by way of illustration and example, embodiments of the present invention are disclosed.

SUMMARY OF THE INVENTION

As used herein, and in the parent patent to which this specification is related, the terms "dentition," "deciduous dentition," "deciduous teeth," "primary teeth," "milk teeth," and "baby teeth," are used interchangeably to refer to one or more human primary teeth.

As used herein, and in the parent patent to which this specification is related, the terms "permanent dentition," "permanent teeth," "secondary teeth," and "adult teeth," are used interchangeably to refer to one or more human secondary teeth.

As used herein, and in the parent patent to which this specification is related, the term "exfoliated" refers to the normal loss of baby teeth after the loss of their root structure.

As used herein, and in the parent patent to which this specification is related, the terms "disinfected" and "decontaminated" are used interchangeably to refer to the cleansing and removal of microorganisms from the tooth.

As used herein, and in the parent patent to which this specification is related, the terms "substantial" and "substantially" mean mostly.

As used herein, and in the parent patent to which this specification is related, the term "bonding agent" refers to the broad category of such bonding agents, and may include one, or a combination of, dental cements, dental adhesives, dental composites, and non-dental epoxies, adhesives, and glues.

As used herein, and in the parent patent to which this specification is related, the terms "jewelry frame," and "jewelry framework" are used interchangeably, and include "bezels" of the type used to hold gemstones, which may be an integral part of the jewelry frame, or that may be separately connected or movably attached to the jewelry frame.

The history of jewelry is as old as the history of man. Styles and trends come and go and come again. What is not found in this history is any event of persons wearing their deciduous teeth, or that of their descendants in the form of jewelry. While the notion sounds barbaric and contrary to civilized norms to some, the inventor believes that it could symbolize the ultimate commitment of love and devotion a parent can have for a child. The symbol exceeds the relevance of personal adornment, much as a Christian wearing a cross.

A primary advantage of the present invention is that it creates a new material form of jewelry. Another advantage of the present invention is that it creates a symbolic means of displaying family commitment in the form of jewelry. Another advantage of the present invention is that it provides multiple and virtually unlimited opportunities to display the symbols. Another advantage of the present invention is that it provides a value added means of keeping family baby teeth. Another advantage of the present invention is that it provides a novel personal material captured in a jewelry frame.

Another advantage of the present invention is that it provides a method of manufacturing jewelry items from deciduous teeth that overcome the several obstacles presented by the small size, small number, variable shape, hollow configuration and brittle consistency of deciduous teeth. Another advantage of the present invention is that it provides a method of strengthening and shaping deciduous teeth so that unique and long lasting jewelry items can be made from the deciduous teeth.

Other advantages of the present invention will become apparent from the following descriptions, taken in connection with the accompanying drawings, wherein, by way of illustration and example, embodiments of the present invention are disclosed.

In one embodiment of the present invention, the deciduous dentition, or primary teeth of one or more children, are provided. The dentition are pulverized into dentition particles. The dentition is disinfected before or after pulverizing. In an optional embodiment, the dentition particles are bleached. In an optional embodiment, the dentition particles are etched. In another optional embodiment, the dentition particles are dyed to obtain a desired color. In an optional embodiment, the dentition is pulverized further into a dentition powder.

In a preferred embodiment, a form, or mold, is provided in the design of the jewelry item desired. The dentition particles are mixed with a chemical bonding agent such as dental cement. The mixture of the dentition particles and chemical bonding agent forms a dentition matrix. The matrix is located within the form. In one embodiment, the form produces a shape similar to a gem stone for mounting in a jewelry article. This will be referred to as a tooth matrix.

As stated above, the term bonding agent is intended to refer to the broad category of such bonding agents, and may include one, or a combination of, dental cements, dental adhesives, dental composites, and non-dental epoxies and glues. These products may be applied in separate steps or collectively to fill voids in a deciduous tooth, or to fill voids between separated portions or particles of one or more of the deciduous teeth, and bond them together as a solid tooth matrix. The various bonding agents may be self-curing, light curing, or a combination thereof. Since the exfoliated deciduous teeth will be used for jewelry, the bonding agent need not be limited to dental grade adhesives, cements or restoration composite resins.

Optionally, an attachment may be located in the matrix to provide a means for attaching the jewelry item to an earring, necklace, bracelet, or the like. Depending on the bonding agent used, specific curing conditions may be recommended to obtain the physical properties desired in the bonded product.

In a preferred embodiment, the matrix is located in a pre-formed jewelry frame. An example of such an item would be a hollow cross. In this manner, the cured matrix would bond to the jewelry frame, securing it in place geometrically, structurally, and/or chemically. This method provides an interference fit potential with the frame to ensure the cured matrix will not dislodge from the frame.

In another preferred embodiment, the deciduous dentition is tumbled into polished dentition particles, larger than a powder. In this embodiment, the dentition particles are mixed or coated with a chemical bonding agent. The mixture of the dentition powder and chemical bonding agent forms the dentition matrix. The matrix is located in a form or pre-formed frame for curing.

The following is a brief summary of a primary embodiment of the present invention for a method of raising funds for an organization. In one embodiment, the organization distributes a solicitation to a buyer, or for delivery to a buyer, by way of a child relative of the buyer. The solicitation comprises an offer to sell a jewelry article made from a processed exfoliated deciduous tooth of the child set in a jewelry object, as a gemstone would be set.

The buyer sends an order for the jewelry article to the manufacturer. The buyer sends a payment for the jewelry article to the manufacturer. The manufacturer sends a payment to the organization, allowing the organization to raise funds for having distributed a solicitation that was converted into a purchase. The manufacturer provides the buyer with a containment system for safe and regulatory compliant shipping of the deciduous tooth from the buyer to the manufacturer. The buyer must send the exfoliated deciduous tooth to the manufacturer. The tooth is evaluated for estimated compatibility with the manufacturing process steps and the jewelry object in which it will be set. If not compatible, the order is rejected. If accepted, the deciduous tooth is processed and set in the buyer's selected jewelry object to create the completed jewelry article.

In another embodiment, the manufacturer certifies that the processed tooth contained in the jewelry article sent to the buyer is the tooth that the buyer sent to the manufacturer.

BRIEF DESCRIPTION OF THE DRAWINGS

The drawings constitute a part of this specification and include exemplary embodiments to the invention, which may be embodied in various forms. It is to be understood that, in some instances, various aspects of the invention may be shown exaggerated, enlarged or otherwise spatially modified to facilitate an understanding of the invention.

FIG. 4 is a chart illustrating approximate eruption of primary and secondary teeth, for which the primary teeth are utilized in the present invention.

DETAILED DESCRIPTION OF THE INVENTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Humans are diphyodont; they develop two sets of teeth during their lives. The first set of teeth are the deciduous teeth; twenty small teeth also known as baby teeth, milk teeth or primary teeth. Deciduous teeth start developing about two months after conception and typically begin to erupt above the gum line when a baby is six or seven months old. Occasionally a baby is born with one or more deciduous teeth, known as natal teeth. By the time a child is six years old, a second set of thirty-two larger teeth, called permanent teeth, start to erupt, or push out of the gums, eventually replacing the deciduous teeth.

Figure 1:
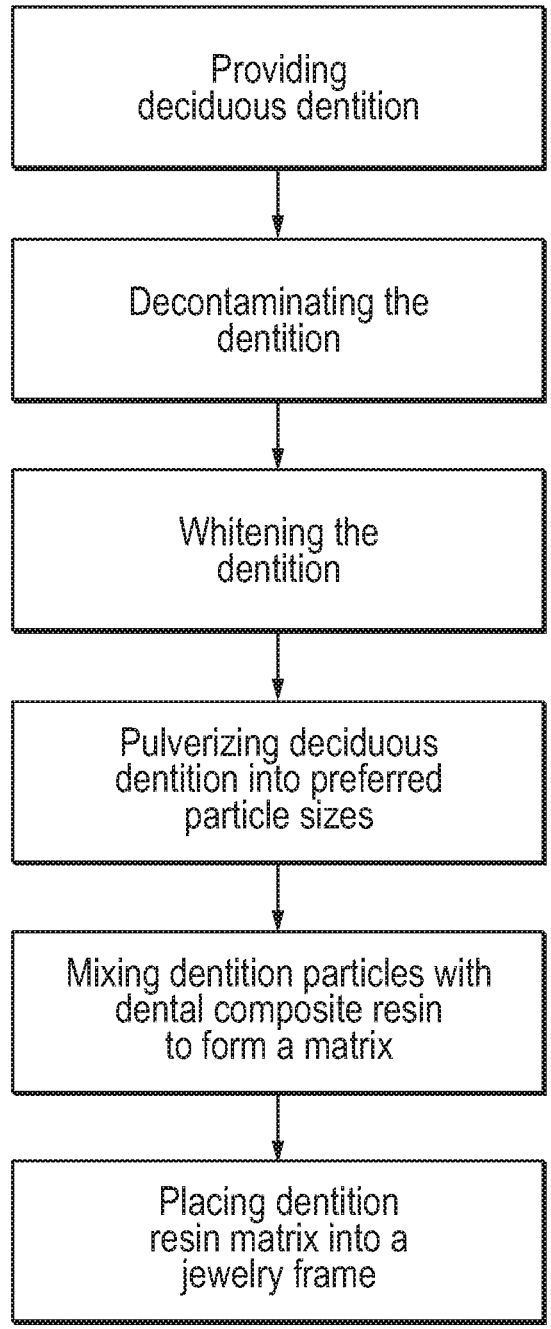
FIG. 1 is a flow chart of one embodiment of the process for making a piece of jewelry made in accordance with a preferred embodiment of the present invention.

FIG. 1 is a flow chart illustrating the steps of creating jewelry in accordance with a preferred embodiment of the present invention. In this Figure, it is seen that the saved teeth may be decontaminated and whitened in separate steps. It is also appreciated that it is possible to accomplish this in a single step by bleaching the dentition. This has the benefit of reducing the rupture strength of the dentition. It is possible to perform the disclosed steps in a different order, such as whitening after pulverizing. It is also possible to add steps, such as for coloring the dentition.

Figure 2:
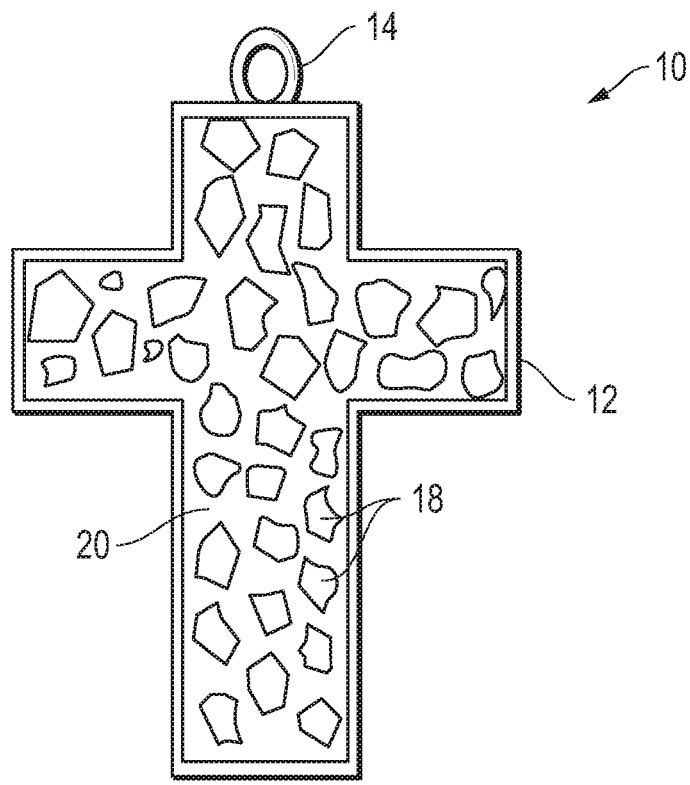
FIG. 2 is an illustration of an example of a piece of jewelry in the shape of a cross with pulverized deciduous dentition cemented in place with a composite resin bonding agent.

FIG. 2 is an illustration of a piece of jewelry made in accordance with a preferred embodiment of the present invention.

Figure 3:
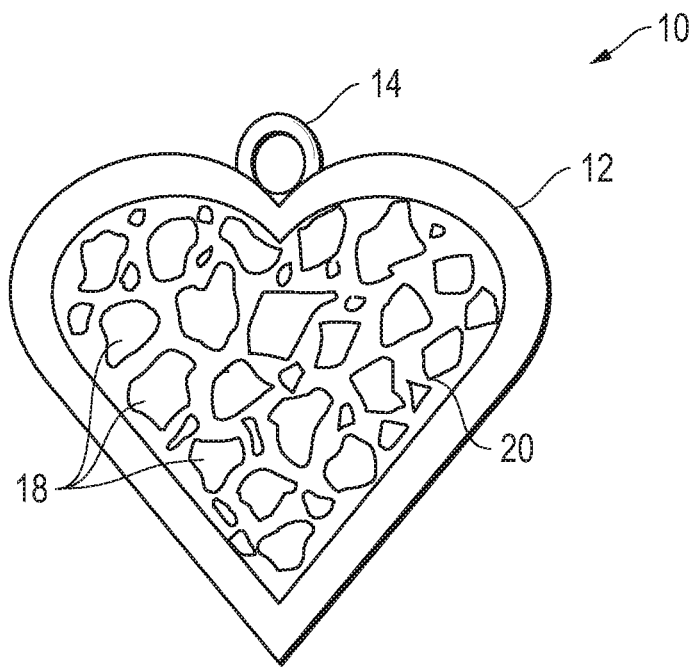
FIG. 3 is an illustration of an example of a piece of jewelry in the shape of a heart with pulverized deciduous dentition cemented in place with a composite resin bonding agent.

FIG. 3 is an illustration of another piece of jewelry made in accordance with a preferred embodiment of the present invention.

In the preferred embodiment of the present invention, the deciduous dentition (one or more primary teeth) of one or more children, are provided. The deciduous dentition is identified and recorded with the person from which they originated and maintained separately from the dentition of others. The dentition should be cleaned of visible blood and debris and kept hydrated in tap water, saline solution, or other preservative solution. Extracted teeth, including deciduous dentition, are considered bio-hazardous waste and must be labeled and handled accordingly.

In a preferred embodiment, the provided dentition are decontaminated. Known methods of storing and sterilizing extracted teeth include steam autoclave, freezing, gamma radiation, numerous liquid chemicals, and gaseous chemicals.

In a preferred embodiment, the exfoliated deciduous teeth are decontaminated, such as by soaking in a chlorine or peroxide based bleaching solution, or by autoclaving. Bleaching decontaminates and whitens the dentition. Additionally, bleaching may soften the dentition, increasing its susceptibility to crushing.

For example, the deciduous teeth may be placed in a sealed specimen container with a sufficient amount of common household bleach (5.25% or 6%), diluted to approximately 1:10 with tap water. In one embodiment, the bleaching solution is a chlorine or peroxide based bleaching solution at appropriate concentration. Higher concentrations reduce the time required to disinfect and whiten the teeth, but also increase the risk of reducing the strength of the teeth.

For example, hydrogen peroxide solution ($H_2O_2$), or sodium hypochlorite (NaOCl) may be used. Hydrogen peroxide is known to be effective at concentrations above approximately 3%.

Sodium hypochlorite is a desirable disinfectant due to its efficacy against pathogenic organisms and pulp digestion. Its concentration for use in conventional endodontic applications varies from 0.5% to 5.25%. At higher concentrations tissue dissolution is better but it also dissolves desirable tissue.

As stated, it will be appreciated that other concentrations and chemical formulations may be used to obtain a satisfactory result. For example, 10% formalin may be used for decontamination and has tissue preservative proprieties.

Alternatively, the dentition may be heat sterilized, as by autoclaving. It is also possible to both autoclave the dentition and separately bleach it for whiteness, as illustrated in FIG. 1.

Thus, while various solutions at various concentrations are capable of disinfecting the exfoliated deciduous teeth, it is the procedural step itself that is important to protect the workers handling the teeth, and to improve the appearance of the final product and the workability of the product by facilitating the removal of pulp related tissue.

For example, in one embodiment in which the teeth are not pulverized, by disinfecting the deciduous teeth, the residual blood and pulp tissue can be removed. This improves the quality of the final product, and importantly, opens the tiny pulp cavity inside the exfoliated tooth so that a bonding agent, such as a solidifying filler can be injected into the pulp cavity. The solidifying filler may be a dental composite of non-dental industry epoxy. In a preferred embodiment, the solidifying filler is colored white, and preferably in a tone and translucence similar to that of the exfoliated deciduous tooth.

As a further example of the benefits provided by the present invention, shaping the solidified tooth matrix may expose contaminants beneath the enamel surface of the tooth. Disinfecting the tooth and filling voids in its structure ensures that the final shaped surface will consist of a clean, color compatible bonding agent, rather than voids and contaminants.

In a first embodiment, the disinfected dentition is then partially pulverized (broken into two or more smaller parts or particles). In one embodiment, the particle sizes obtained are between −2 and 2 on the PHI particle scale. This preferred range of particle size retains the natural appearance and recognition of the deciduous teeth, but reduces it to a size small enough to position the particles within the space of a jewelry framework for cementing. In an optional embodiment, the dentition is pulverized into a fine powder form. The powder may be mixed with larger particles to create a solid appearance to the article when reconstituted in a desired shape.

In an alternative embodiment, the exfoliated and pulverized pieces of deciduous teeth are disinfected after they are broken.

The dentition may also be etched with a chemical, such as a phosphoric acid gel. The etching, if performed, roughens the surface of the particles, increasing the surface area and improving the adherence of the dental cement (or other bonding agent) to the particle surfaces. Etching may be performed before or after pulverization. In another optional embodiment, the dentition particles (or powder) are dyed to obtain a desired color.

In a preferred embodiment, a form, or mold, is provided in the design of the jewelry item desired. The dentition particles are mixed with a chemical bonding agent, such as dental cement or dental composite resin. Dental composite resins are types of synthetic resins known in the dental profession as restorative materials or adhesives. These bonding agents are used for the repair of teeth and the construction of artificial teeth and are designed for attachment to tooth enamel.

The mixture of the dentition particles and the chemical bonding agent (such as a dental composite resin, or other bonding agent) forms a dentition-adhesive matrix. The matrix is placed within the form so as to fill the void of the mold.

Optionally, a jewelry attachment may be located in the matrix to provide a means for attaching the jewelry item to an earring, necklace, bracelet, or the like. Depending on the bonding agent used, specific curing conditions may be recommended to obtain the physical properties desired in the bonded product.

Curing of resins containing a photoinitiator is accelerated by exposure to light, such as ultraviolet light. For example, bonding agents containing compounds, such as amorphous calcium phosphate (ACP) agents, are light-cured bonding adhesives. Precise curing procedures depend on the bonding agent selected.

In one embodiment, the matrix is located in a pre-formed jewelry frame. An example of such an item would be the frame of a religious article, such as a cross. The frame is preferably a hollow metal structure. In this manner, the matrix would bond to the jewelry frame, securing it in place geometrically and/or bonding chemically. This method provides an interference fit potential with the frame to ensure the cured matrix will not dislodge from the frame.

In an alternative embodiment, the dentition particles are located in the mold first, and the adhesive is then introduced into the mold to fill the voids between the pulverized dentition particles.

In another preferred embodiment, the deciduous dentition is partially crushed into a powder. In this embodiment, the dentition powder is mixed or coated with a chemical bonding agent prior to introduction into the mold. The mixture of the dentition powder and chemical bonding agent forms the dentition matrix, which is then located into a mold form or pre-formed frame for curing.

In another preferred embodiment, the deciduous dentition is tumbled into polished dentition particles, larger than a powder. In this embodiment, the dentition particles are mixed or coated with a chemical bonding agent. The mixture of the dentition powder and chemical bonding agent forms the dentition matrix. The matrix is located in a form or pre-formed frame for curing.

It is known that deciduous teeth are very dissimilar to permanent teeth in a number of ways beyond the obvious size and number differences. In particular, whereas permanent teeth removed from the host may be dense and solid with extended roots, exfoliated deciduous teeth will likely have a lower density, comprising only a hollow crown due to natural resorption of the roots. Residual pulp tissue and blood stains may remain in the pulp cavity, making it difficult to remove.

Exfoliated deciduous teeth may also have surface fissures that increase the brittleness of the teeth, and susceptibility to staining in the presence of dyes or other chemicals. The deciduous teeth may have other defects and inclusions that are difficult to see.

The presently disclosed embodiment provides new procedures for adapting to these several complexities of deciduous teeth, and use them advantageously to provide new jewelry articles.

FIG. 4 is a chart illustrating approximate eruption of primary and secondary teeth, for which the primary teeth are utilized in the present invention. The average child has only twenty primary teeth, including just eight primary molars.

Figure 5:
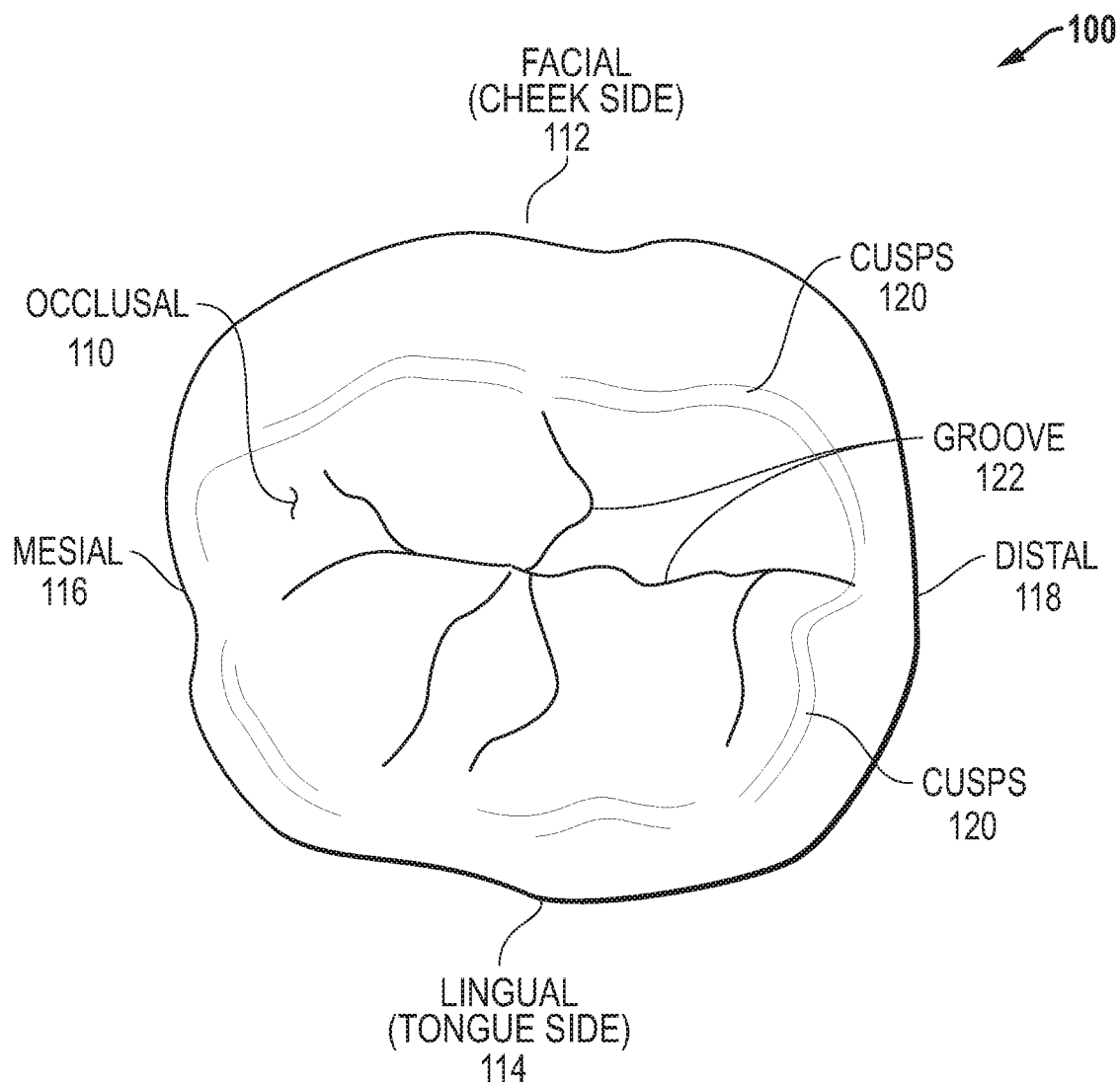
FIG. 5 is an occlusal side view of an exfoliated deciduous molar tooth, identifying various surfaces and structure of the deciduous molar.

FIG. 5 is a top view representation of an exfoliated deciduous molar tooth 100. All that remains of molar 100 is the crown portion and a thin neck portion 132 (See FIG. 6) that formerly connected the crown to the roots.

In FIG. 5, molar 100 is viewed substantially towards an occlusal side 110, and identifying other surfaces of molar tooth 100. From this view it is seen that molar 100 has a facial side 112 and an opposite lingual side 114 which is the side adjacent to the tongue. A mesial side 116 is the side of tooth 100 that faces the front of the mouth and center of the face. The distal side 118 is the side of tooth 100 that faces opposite to mesial side 116, and towards the back of the mouth. These five sides form the crown of molar 100.

Occlusal side 110 is used for chewing food. Occlusal side 110 has an irregular surface formed by grooves 122 extending between cusps 120. Cusps 120 are the highest points of occlusal side 110. Grooves 122 form the lowest points on occlusal side 110.

Figure 6:
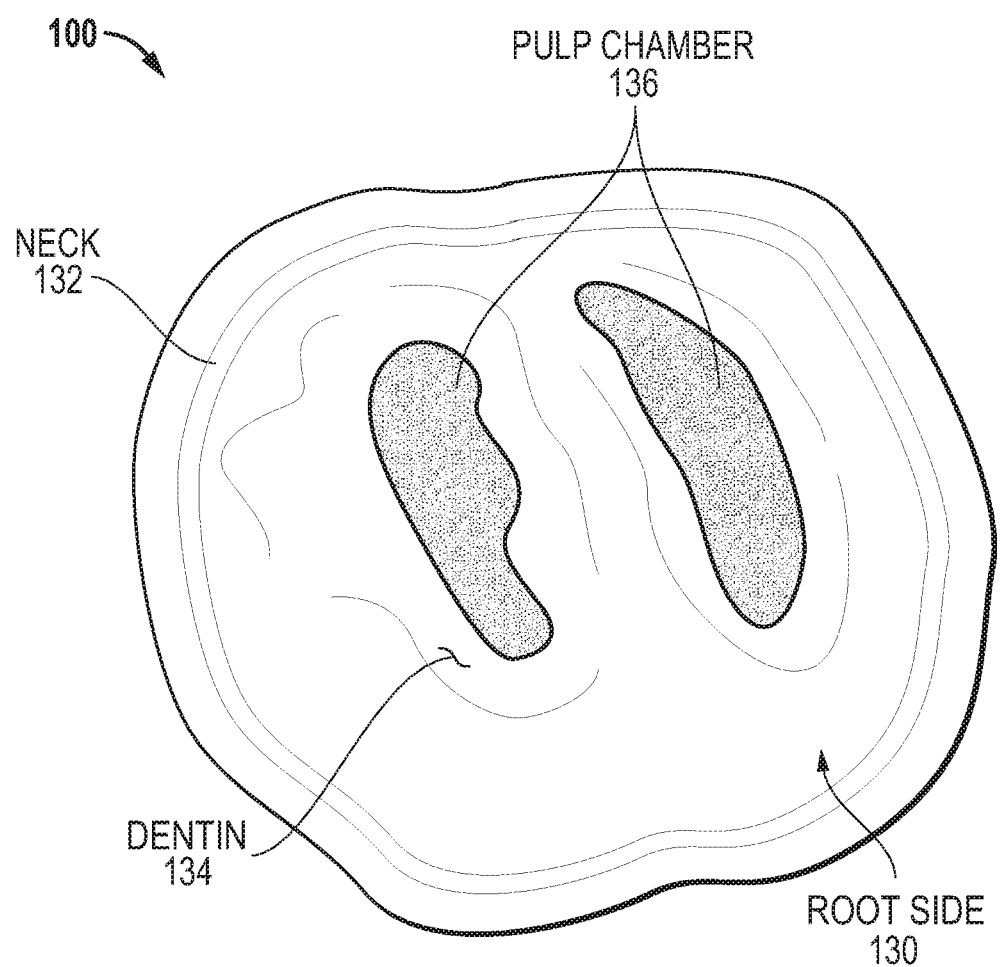
FIG. 6 is a view of the exfoliated deciduous molar tooth, illustrated from the root-side view, opposite of the occlusal side view of FIG. 5, and identifying the structural features of the tooth.

FIG. 6 is a root-side 130 view of the exfoliated deciduous molar tooth 100, being illustrated from the side opposite occlusal side 110. Root-side 130 has no roots, since the roots of deciduous teeth are resorbed by the body as part of the exfoliation process. The interior of molar 100 is substantially hollow. Hollow pulp chambers 136 are surrounded by dentin 134. When exfoliated, some tissue and blood is likely to be found in pulp chamber 136 on root-side 130, where the crown detached from the resorbed roots at neck 132.

Figure 7:
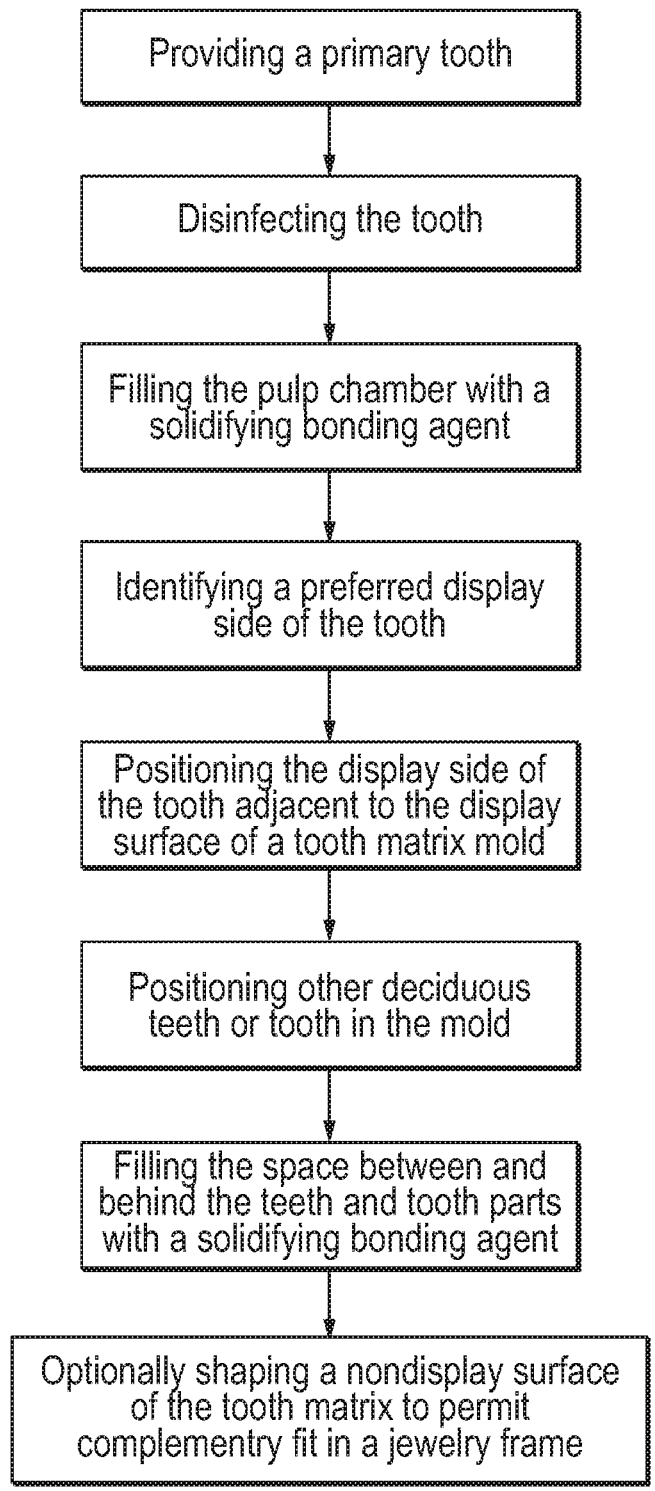
FIG. 7 is a flow chart disclosing an alternative process for creating a piece of jewelry in which a display face is formed from multiple tooth parts.
Figure 11:
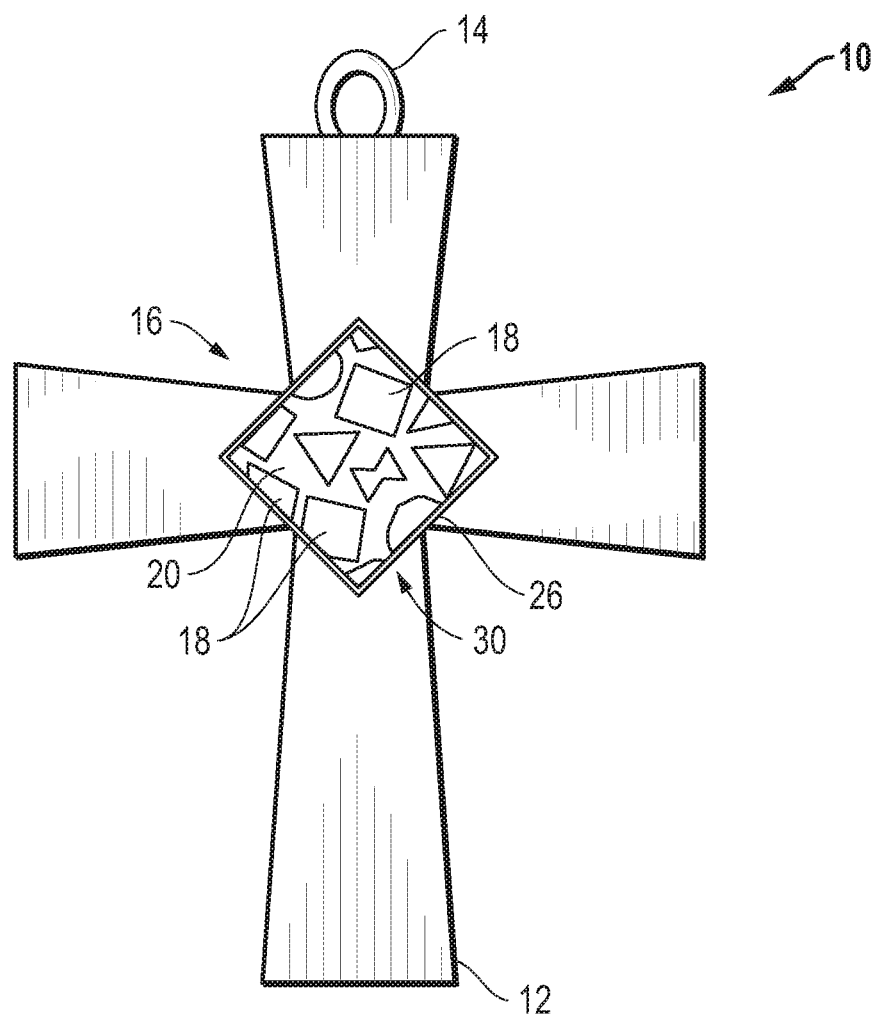
FIG. 11 is a front view of a jewelry article having a shaped tooth matrix attached to a jewelry frame, in which the tooth matrix has a display surface comprised of tooth particle bonded together with a solidifying bonding agent.
Figure 12:
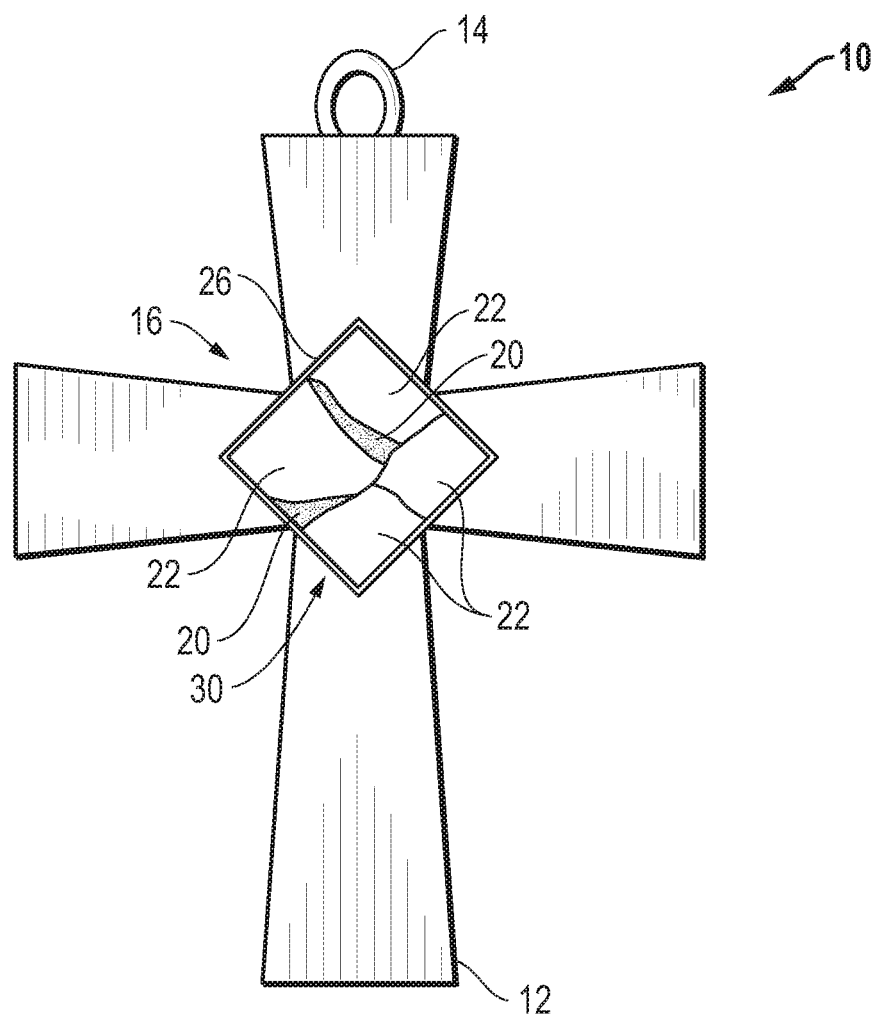
FIG. 12 is a front view of a jewelry article having a shaped tooth matrix attached to a jewelry frame, in which the tooth matrix is comprised of multiple deciduous teeth or tooth parts bonded together with a solidifying bonding agent.

FIG. 7 is a flow chart outlining an alternative process for manufacturing a jewelry article in which a display surface 30 (FIGS. 11-13) is formed from teeth 22 (FIGS. 11-12). Teeth 22 may be advantageously mixed with smaller tooth parts 18 in this embodiment (not shown). In this embodiment, deciduous teeth (one or more primary teeth) of one or more children, are provided. The deciduous tooth obtained is disinfected in accordance with any of the procedures disclosed herein, or by any other generally accepted procedure. In the next step, pulp chamber 136 is filled with bonding agent 140 (FIGS. 11-12). Bonding agent 140 is then cured to form a solid tooth matrix 16. Bonding agent 140 may be light cured, self-curing, or a combination thereof.

Solid tooth matrix 16 is now comprised of a display surface 30 and non-display sides (not shown) behind and around display surface 30, and forming the remainder of the exterior of tooth matrix 16. If solid tooth matrix 16 has not been molded to its final shape, a non-display side of tooth matrix 16 is then shaped such as by cutting, sanding, or polishing until tooth matrix 16 obtains the shaped required for complementary fit into jewelry frame 12. Such fit may be into a bezel 26 that is either integral with, or connectable to jewelry frame 12.

The shaping of tooth matrix 16 may be performed by hand, but the present invention advantageously increases the strength of tooth parts 18 and teeth 22 such that tooth matrix 16 can be readily machined using conventional lapidary equipment and technology.

Figure 8:
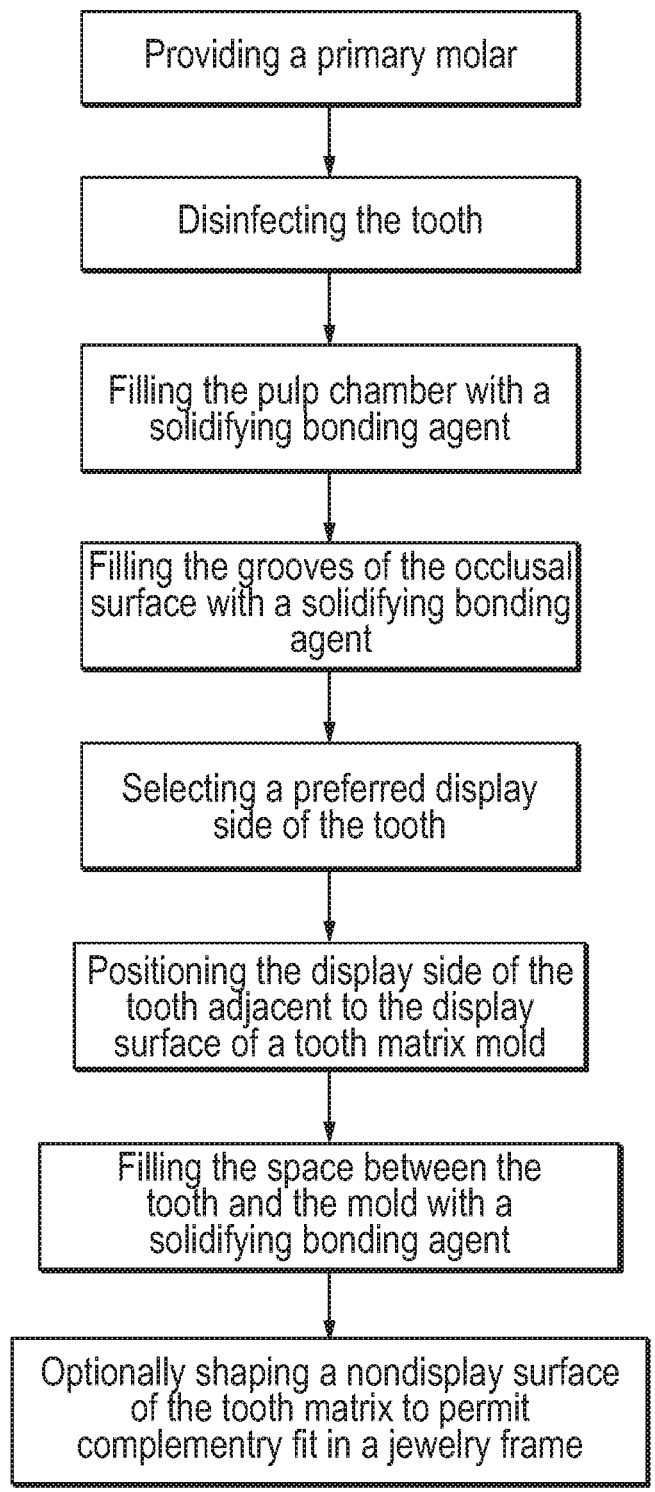
FIG. 8 is a flow chart disclosing an alternative process for creating a piece of jewelry in which the pulp chambers are filled with a bonding agent.
Figure 10:
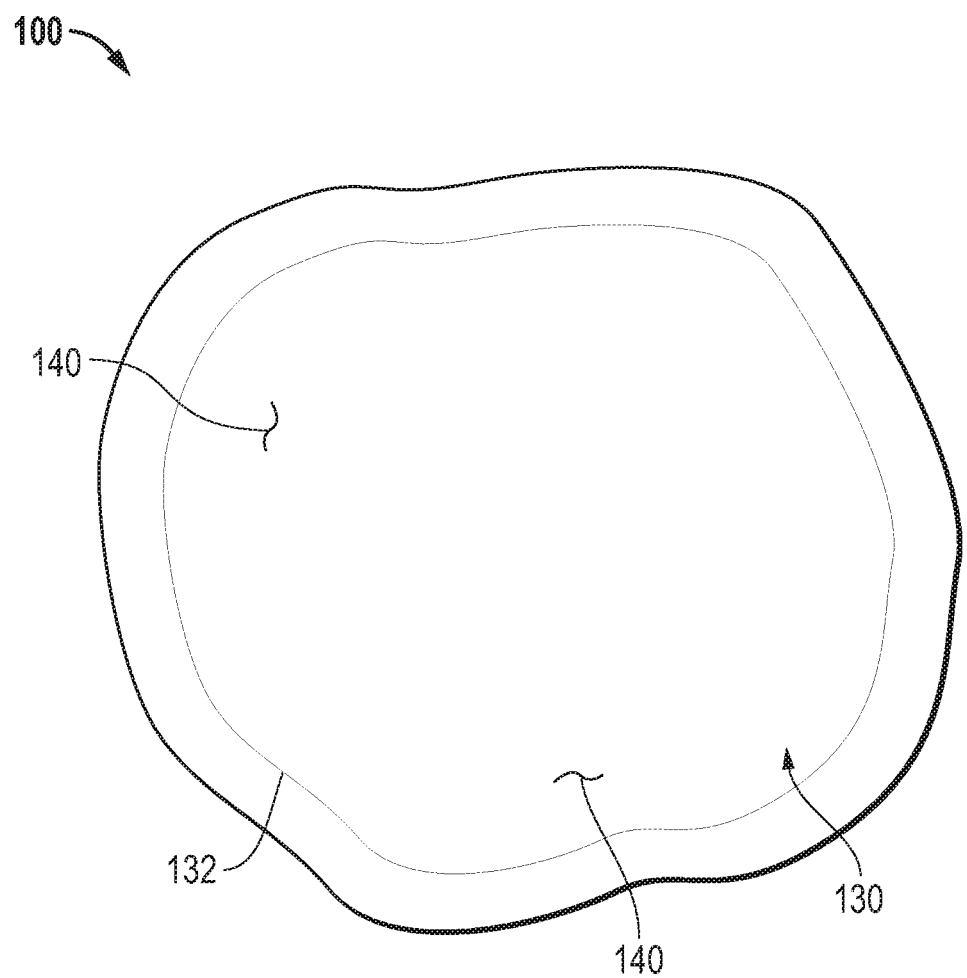
FIG. 10 is a drawing of the primary molar of FIG. 6, as viewed from the root-side, illustrating the pulp chambers substantially filled with a solidifying bonding agent in accordance with an embodiment of the present invention.

FIG. 8 is a flow chart outlining an alternative process for manufacturing jewelry articles in which a deciduous molar 100 is used to provide the display surface 30. In this embodiment, a deciduous molar tooth 100 is provided. Molar 100 is disinfected in accordance with any of the procedures disclosed herein, or by any other generally accepted procedure. In a subsequent step, pulp chamber 136 is filled with bonding agent 140 (FIGS. 6 and 10). Bonding agent 140 is then cured to form a solid tooth matrix 16.

Figure 9:
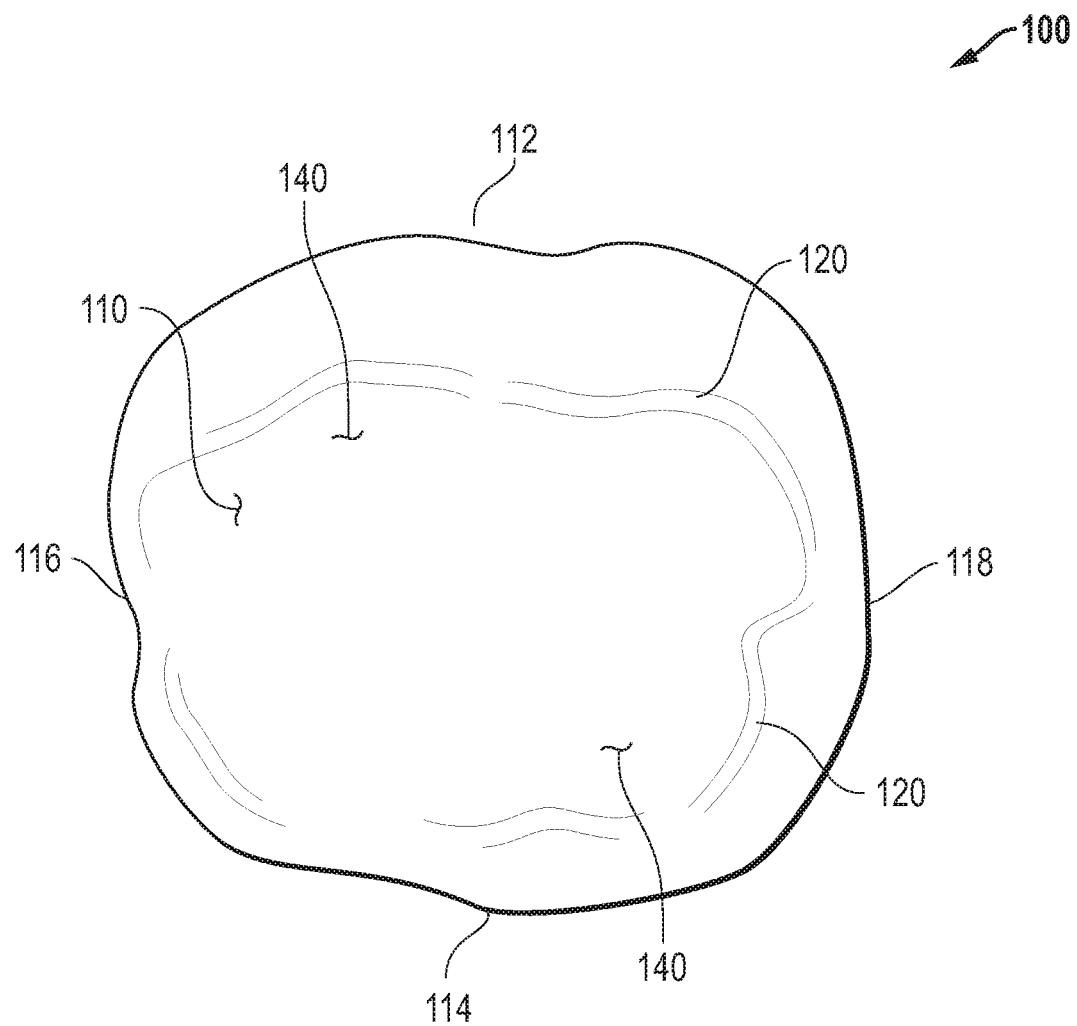
FIG. 9 is a drawing of the primary molar of FIG. 5, as viewed from the occlusal side, and illustrating the grooves substantially filled with a solidifying bonding agent in accordance with an embodiment of the present invention.

Bonding agent 140 may be light cured, self-curing, or a combination thereof. In another step which may be performed before or coincident with the step of filling of pulp chamber 136, grooves 122 of occlusal side 110 are substantially filled with bonding agent 20 (FIGS. 5 and 9). Bonding agent 140 is then cured to form a solid tooth matrix 16. Bonding agent 140 may be light cured, self-curing, or a combination thereof. In filling pulp chamber 136 and groove 122, bonding agent 140 may be added in layers, and cured between adding layers. This is beneficial in light activated curing to assure complete curing of the bonding agent. Also, additional tooth parts 18 may be added prior to adding a layer of bonding agent 140, to strengthen the tooth matrix 16 and increase the concentration of tooth matter in the tooth matrix 16.

Figure 13:
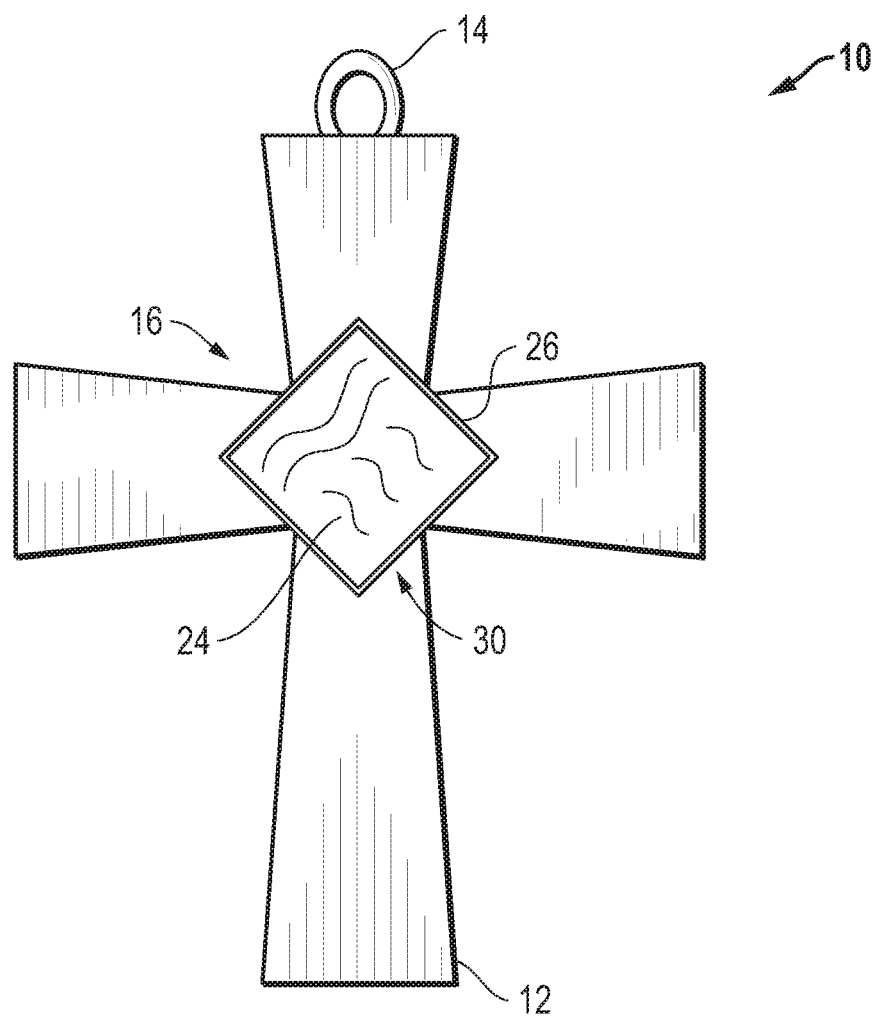
FIG. 13 is a front view of a jewelry article having a shaped deciduous tooth attached to a jewelry frame. In this embodiment, a surface of the tooth was selected as the display surface.

As best seen in FIG. 13, a preferred display side 24 of the tooth is selected. As shown in FIG. 13, solidified tooth matrix 16 may have a single tooth side 24 selected to be the display surface 30.

If sufficiently large, tooth matrix 16 (shown in FIGS. 11-13) may be shaped for connection to jewelry frame 12 such as by using conventional lapidary techniques and equipment. Shaped tooth matrix 16 is then bonded to jewelry frame 12 with bonding agent 140. For connection to jewelry frame 12, a simple adhesive or glue type bonding agent 140 may be used.

If tooth matrix 16 (shown in FIGS. 11-13) is not large enough for shaped connection to jewelry frame 12, it may be built-up with additional bonding agent 140 and optionally with additional tooth parts 18. In this method, selected display side 24 is positioned in a mold (jewelry frame 12) adjacent to the position of display surface 30 of the mold. Bonding agent 140 is placed (by injection or other means) between the mold and tooth matrix 16 and cured to provide a solid tooth matrix 16 that may be shaped for, or if properly shaped, directly connected to jewelry frame 12.

It will be recognized by one of ordinary skill in the art that the procedural steps generally outlined in FIGS. 7 and 8 may be performed in other sequences and the same desired results may be achieved.

In another embodiment, a doping stick can be attached to tooth matrix 16 on the side opposite display surface 30 to improve handling of solidified tooth matrix 16 during shaping procedures.

FIG. 9 is a drawing of occlusal side 110 of primary tooth molar 100, illustrating groove 122 substantially filled with solidified bonding agent 140, and made in accordance with the manufacturing procedures of the present invention detailed above.

FIG. 10 is a drawing of root-side 130 of primary tooth molar 100, illustrating pulp chambers 136 substantially filled with solidified bonding agent 140, and made in accordance with the manufacturing procedures of the present invention detailed above. In the illustration shown, some or all of the exposed portion of dentin 134 (See FIG. 6) has also been covered by bonding agent 140. The covering of all or part of dentin 134 is optional.

FIG. 11 is a front view of a jewelry article 10 having a solidified tooth matrix 16. Tooth matrix 16 is comprised of deciduous tooth parts 18 and a solidified bonding agent 20 interspersed between deciduous tooth parts 18. Bonding agent 20 bonds tooth parts 18 together and fills voids between tooth parts 18 to form a solid tooth matrix 16. This embodiment may be manufactured in accordance with the procedures disclosed in U.S. Pat. No. 8,226,877, and may include the additional shaping procedures identified herein.

In the embodiment illustrated, tooth matrix 16 is rectilinear in shape, providing pairs of parallel sides connected by a display surface 30, which is viewed from the front when looking directly at jewelry article 10. In the embodiment illustrated, tooth matrix 16 is shaped for complementary attachment to a bezel 26, which is an integral component of jewelry frame 12 of the particular jewelry article 10.

Tooth matrix 16 may be formed and solidified in a remote mold, or in jewelry frame 12 itself. In a preferred embodiment, tooth parts 18 are prearranged in the mold to create the most desirable display surface 30. The desirability of display surface 30 may depend upon the size, shape, quality, color, and collective arrangement of tooth parts 18. The desirability of display surface 30 also depends on maximizing the surface percentage of tooth parts 18 to bonding agent 20.

The desired surface of tooth parts 18 will normally not include the root-side 130. In a molar, the preferred display sides are often, but not exclusively, facial side 112 and lingual side 114.

When tooth parts 18 are relatively small, they may be arranged randomly to form display surface 30. When tooth parts 18 are larger, prearrangement becomes increasingly significant to the aesthetic quality of jewelry article 10. For example, prearrangement of large tooth parts 18 can minimize the percentage of bonding agent 20 visible on display surface 30 of tooth matrix 16.

In one embodiment, deciduous tooth parts 18 are substantially disinfected before bonding. This improves the color and quality of jewelry article 10, and provides a safe working environment for the manufacturer of jewelry article 10.

In one embodiment, disinfected tooth parts 18 are arranged (deliberately or randomly) to form display surface 30. Bonding agent 20 is then applied to the back side of tooth parts 18. A low viscosity bonding agent is preferred so as to penetrate the small spaces between tooth parts 18. Bonding agent 20 is then cured to form a solid tooth matrix 16. Bonding agent 20 may be light cured, self-curing, or a combination thereof.

In one embodiment, bonding agent 20 is applied in layers, with a curing step between layers to ensure solidification. In another embodiment, additional tooth parts 18 are added prior to adding a layer of bonding agent 20. This process adds hardness to tooth matrix 16, and accomplishes the desirable result of increasing the relative concentration of deciduous tooth material in tooth matrix 16. This procedure is adaptable to any of the embodiments disclosed herein.

In one embodiment, bonding agent 20 is colored white to blend with tooth parts 18. In one embodiment, bonding agent 20 is a dental composite. In one embodiment, bonding agent is a commercial epoxy. In one embodiment, bonding agent 20 is substantially transparent. In an alternative embodiment bonding agent 20 is colored to contrast with tooth parts 18.

Solid tooth matrix 16 is comprised of a display surface 30 and non-display sides (not shown) behind and around display surface 30, and forming the remainder of the exterior of tooth matrix 16. If solid tooth matrix 16 has not been molded to its final shape, a non-display side of tooth matrix 16 is then shaped such as by cutting, sanding, or polishing until tooth matrix 16 obtains the shape required for complementary fit into jewelry frame 12. Such fit may be into a bezel 26 that is either integral with, or connectable to jewelry frame 12.

Shaping tooth matrix 16 may be performed by hand, but the present invention advantageously increases the strength of tooth parts 18 such that tooth matrix 16 can be readily machined using conventional lapidary equipment and technology. In one embodiment, display surface 30 of tooth matrix 16 is polished.

FIG. 12 is a front view of jewelry article 10 having a shaped tooth matrix 16 attached to bezel 26 of jewelry article 10. In this embodiment, tooth matrix 16 is comprised of multiple deciduous teeth 22 and may further include tooth parts 18 (not illustrated), bonded together with solidified bonding agent 20. This embodiment may be manufactured in accordance with the procedures disclosed in U.S. Pat. No. 8,226,877, and may include the additional procedures identified herein, and particularly as outlined in FIG. 7.

In one embodiment, pulp chamber 136 of tooth 22 is filled with bonding agent 20 to increase the strength and eliminate voids in tooth 22 (See FIG. 7). This process reduces the likelihood that tooth 22 will break apart when machined, and eliminates voids when tooth 22 is shaped beyond the enamel or dentin structure.

In the embodiment illustrated, tooth matrix 16 is rectilinear in shape, providing pairs of parallel sides connected by a display surface 30, which is viewed from the front when looking directly at jewelry article 10. In the embodiment illustrated, tooth matrix 16 is shaped for complementary attachment to a bezel 26, which is an integral component of jewelry frame 12 of the particular jewelry article 10. Other shapes, such as hearts, circles and ovals can also be produced.

Tooth matrix 16 may be formed and solidified in a remote mold, or in jewelry frame 12 itself. In one embodiment, a display side of a tooth 22 is selected. The display side of teeth 22 will normally not include the root-side 130. In a molar, the preferred display sides are often, but not exclusively, facial side 112 and lingual side 114, as they are the larger surfaces.

Selected display side of a tooth 22 is positioned adjacent to the location of display surface 30 in the mold (or frame 12). This helps to create the most desirable display surface 30. Tooth parts 18 may be added to fill in any space between teeth 22. This has the desirable effect of increasing the ratio of tooth 22 and tooth part 18 to bonding agent 20 at display surface 30, minimizing the amount of bonding agent 20 visible on display surface 30.

In one embodiment, deciduous teeth 22 are substantially disinfected before placement in the mold or frame. This improves the color and quality of jewelry article 10, and provides a safe working environment for the manufacturer of jewelry article 10.

In one embodiment, a disinfected tooth 22 is positioned such that a selected display side of tooth 22 adjacent to the display surface and one or more tooth parts 18 are arranged to form display surface 30. Bonding agent 20 is then applied to the back side of teeth 22 (and tooth parts 18 if present). A low viscosity bonding agent is preferred so as to penetrate the small spaces between teeth 22 and tooth parts 18. Bonding agent 20 is then cured to form a solid tooth matrix 16. Bonding agent 20 may be light cured, self-curing, or a combination thereof.

In one embodiment, bonding agent 20 is applied in layers, with a curing step between layers to ensure solidification. In another embodiment, tooth parts 18 are added after curing of a layer of bonding agent 20. This process adds hardness to tooth matrix 16, and accomplishes the desirable result of increasing the relative concentration of deciduous tooth material in tooth matrix 16.

In a preferred embodiment, bonding agent 20 is colored white to blend with teeth 22. Bonding agent 20 may be a dental composite or commercial epoxy or other bonding agent suitable to adhere to the enamel of teeth 22. In one embodiment, bonding agent 20 is substantially transparent, providing a different appearance in which the tooth material is distinguishable from bonding agent 20. In an alternative embodiment bonding agent 20 is colored to contrast with tooth parts 18.

Solid tooth matrix 16 is comprised of a display surface 30 and non-display sides (not shown) behind and around display surface 30, and forming the remainder of the exterior of tooth matrix 16. If solid tooth matrix 16 has not been molded to its final shape, a non-display side of tooth matrix 16 is then shaped such as by cutting, sanding, or polishing until tooth matrix 16 obtains the shape required for complementary fit into jewelry frame 12. Such fit may be into a bezel 26 that is either integral with, or connectable to jewelry frame 12.

Shaping tooth matrix 16 may be performed by hand, but the present invention advantageously increases the strength of tooth parts 18 such that tooth matrix 16 can be readily machined using conventional lapidary equipment and technology. In one embodiment, display surface 30 of tooth matrix 16 is polished.

FIG. 13 is a front view of jewelry article 10 having a shaped tooth matrix 16 attached to bezel 26 of jewelry article 10 In this embodiment, a single surface 24 of a deciduous tooth was selected as display surface 30. This embodiment may be manufactured in accordance with the procedures disclosed in U.S. Pat. No. 8,226,877, and may include the additional shaping procedures identified herein, and particularly as outlined in FIG. 8, although it is not required that deciduous molar 100 be used to achieve a display surface from a single deciduous tooth. Other deciduous teeth, such as the incisors and cuspids (canine teeth) may also be used in this manner, but they will provide a smaller tooth matrix 16 as a result of their smaller size.

In one embodiment, pulp chamber 136 of molar 100 (or other tooth 22) is filled with bonding agent 140 to increase the strength and eliminate voids in tooth 100, 22 (See FIG. 8). In another step which may be performed before or coincident with the step of filling pulp chamber 136, grooves 122 of occlusal side 110 are substantially filled with bonding agent 140 (FIGS. 5 and 9). Bonding agent 140 is then cured to form a solid tooth matrix 16. Bonding agent 140 may be light cured, self-curing, or a combination thereof.

This process reduces the likelihood that molar 100 or tooth 22 will break apart when machined, and eliminates voids when molar 100 or tooth 22 is shaped beyond the enamel or dentin structure.

In this embodiment, and as can be seen in FIG. 13, tooth matrix 16 may have a single tooth side 24 serving as display surface 30. In another embodiment, a doping stick can be attached to tooth matrix 16 on the side opposite display surface 30 to improve handling of solidified tooth matrix 16 during shaping procedures. The doping stick may be attached to tooth matrix 16 with an appropriate bonding agent 20. This embodiment is adaptable for any embodiment disclosed herein.

In the embodiment illustrated, tooth matrix 16 is rectilinear in shape, providing pairs of parallel sides connected by a display surface 30, which is viewed from the front when looking directly at jewelry article 10. In the embodiment illustrated, tooth matrix 16 is shaped for complementary attachment to a bezel 26, which is an integral component of jewelry frame 12 of the particular jewelry article 10. Other shapes, such as hearts, circles and ovals can also be produced.

If filled molar 100 lacks the size or geometry for complementary fit into jewelry frame 12, a larger tooth matrix 16 of the desired geometry may be formed and solidified in a remote mold, or in jewelry frame 12 itself. In one embodiment, deciduous molar 100 or other tooth 22 is substantially disinfected before placement in the mold or frame 12. This improves the color and quality of jewelry article 10, and provides a safe working environment for the manufacturer of jewelry article 10.

In one embodiment, display side 24 of molar 100 is selected. Display side 24 of molar 100 will normally not be root-side 130. In a molar, the preferred display sides are often, but not exclusively, facial side 112 and lingual side 114, as they are the larger and smoother surfaces.

Display side 24 of disinfected molar 100 is positioned adjacent to the location of display surface 30 in the mold (or frame 12). This helps to create the most desirable display surface 30. Tooth parts 18 may be added to fill in any space between the mold and molar 100. Tooth parts may also be added to bonding agent 140 when filling pulp chamber 136 and grooves 122. This has the desirable effect of increasing the ratio of tooth material and tooth parts 18 to bonding agent 140.

Bonding agent 140 is then applied to the back side of molar 100, opposite display side 24. A low viscosity bonding agent is preferred so as to penetrate the small spaces between molar 100 and any tooth parts 18. Bonding agent 140 is then cured to form a solid tooth matrix 16. Bonding agent 140 may be light cured, self-curing, or a combination thereof.

In one embodiment, bonding agent 140 is applied in layers, with a curing step between layers to ensure solidification. In another embodiment, tooth parts 18 are added after curing of a layer of bonding agent 140. As before, this process adds hardness to tooth matrix 16, and accomplishes the desirable result of increasing the relative concentration of deciduous tooth material in tooth matrix 16.

Bonding agent 140 may be a dental composite or commercial epoxy or other bonding agent suitable to adhere to the enamel of teeth 22. In each embodiment disclosed herein, tooth 100, 22 or tooth parts 18, may be etched prior to bonding, as disclosed in U.S. Pat. No. 8,226,877.

At this procedural point, filled molar 100 forms a solid tooth matrix 16 having a display side 24 at display surface 30, and non-display sides (not shown) behind and around display surface 30, forming the remainder of the exterior of tooth matrix 16. If tooth matrix 16 has not been molded to its final shape, a non-display side of tooth matrix 16 is then shaped such as by cutting, sanding, or polishing until tooth matrix 16 obtains the shaped required for complementary fit into jewelry frame 12. Such fit may be into a bezel 26 that is either integral with, or connectable to jewelry frame 12.

Shaping tooth matrix 16 may be performed by hand, but the present invention advantageously increases the strength of tooth parts 18 such that tooth matrix 16 can be readily machined using conventional lapidary equipment and technology. In one embodiment, display side 24 of molar 100 is polished.

As illustrated in the embodiments outlined in FIGS. 7 and 8, and as further detailed in FIGS. 11-13, tooth matrix 16 replaces traditional gemstones in placement in jewelry article 10. The disclosed procedures for forming tooth matrix 16 create a deciduous tooth-based product that is machinable by use of conventional lapidary shaping equipment and techniques performed on gemstones.

In an alternative embodiment to those illustrated in FIGS. 11-13, jewelry frame 12 may have prongs for holding tooth matrix 16 in place, or by any other means by which a conventional gemstone is secured to a jewelry frame.

A novel aspect of the invention is that the filled and shaped deciduous teeth 22 (See FIGS. 12 and 13) and tooth matrices 16 (FIGS. 11-13) are displayed materially, but not in their natural geometry. Their aesthetic appeal is derived from the recognition of the material and color in a subtle form that is intentionally contrasted from their normal geometric structure. The subtle association of the jewelry article 10 to the family member who yielded the deciduous teeth enhances the value of the jewelry article 10, which is unlike any other available before the disclosure of the present invention.

It will be understood by one of ordinary skill in the art that the disclosures related to the various figures and embodiments can be mixed and matched to obtain desired results.

In another embodiment, (not illustrated) the foregoing disclosures related to the various figures and embodiments are applied to a keepsake article that is not worn on the body. In this embodiment, one or more deciduous teeth are provided and disinfected. The deciduous teeth are broken into multiple parts. An inlay relief is formed on the keepsake article, such as a jewelry box. The tooth parts are located in the inlay relief. A solidified bonding agent 40 is interspersed between the tooth parts 18 to form a solid tooth matrix 16 inlay on the keepsake article.

Figure 14:
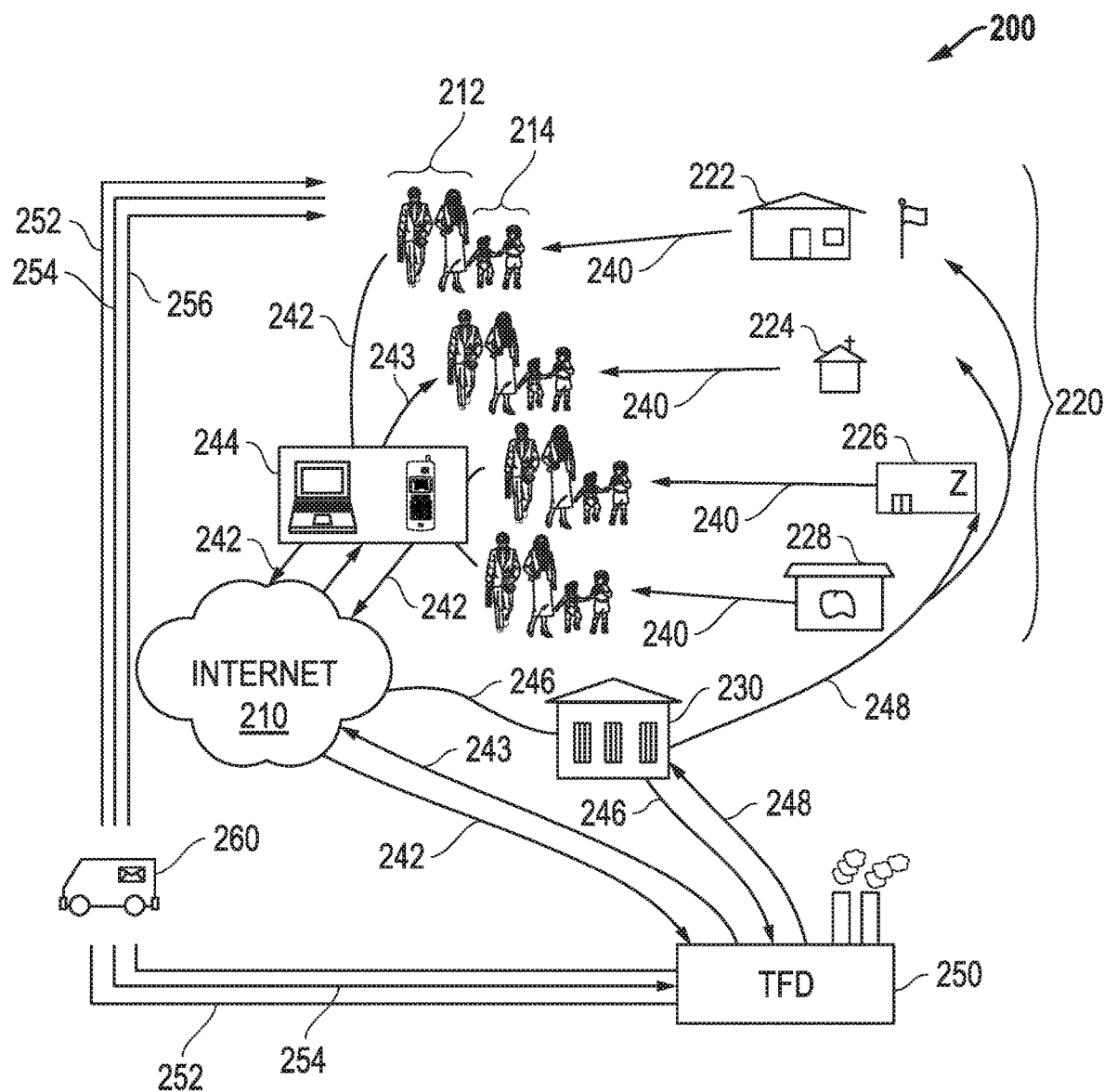
FIG. 14 is a schematic of the process for raising funds disclosed in the present invention, which relies in part on the processes and products disclosed herein and in the related patent and application identified above.

FIG. 14 is a schematic for the method of raising funds for an organization disclosed in the present invention. As shown in FIG. 14, parents and caretakers (buyers) 212 of children 214 are shown. Organizations 220 are also illustrated. Typical organizations are shown as schools 222. Schools 222 may be public or private, secular or nonsecular. Also shown are charitable and religious organizations 224. Also shown are social organizations 226. Also shown are professional organizations, such as dental clinics 228.

In a first step of the method, a solicitation is distributed 240 through the organization 220 to a buyer 212. This may be provided for delivery to a buyer 212 by a child 214. Buyer 212 is a relative or custodian of child 214. The solicitation comprises an offer to sell a jewelry article. The jewelry article comprises a processed exfoliated deciduous tooth of child 214 set in a metallic jewelry object.

In a second step of the method, an order for the jewelry article is sent 242 from the buyer 212 to the manufacturer 250. This may be advantageously sent by a computer or cell phone 244 through the Internet 210 to manufacturer 250. As a component of order 242, a payment transaction 246 for the jewelry article is authorized by buyer 212 as payable to manufacturer 250. Payment transaction 246 transacting payment to manufacturer 250 may be authorized and processed through one or more financial institutions 230 including a bank, credit card company, or online payment processor over the Internet 210.

In a third step of the method, a payment transaction 248 for the successful solicitation of a sale is authorized by manufacturer 250 as payable to organization 220. Payment transaction 248 transacting payment to organization 220 may be authorized and processed through one or more financial institutions 230 including a bank, credit card company, or online payment processor over the Internet 210.

In a fourth step of the method, manufacturer 250 delivers 252 a nesting container system for receiving the exfoliated deciduous tooth of child 214 of buyer 212. The delivery 252 may be made by any convenient means, such as by postal mail 260.

In a fifth step of the method, buyer 212 delivers 254 one or more exfoliated deciduous teeth to manufacturer 250 inside the container system provided by manufacturer 250. The delivery 254 may be made by any convenient means, such as by postal mail 260.

One embodiment of the invention includes the additional step of evaluating the deciduous tooth prior to processing, and accepting or rejecting order 242 based on compatibility of the deciduous tooth with processing requirements.

Another embodiment of the invention includes the additional step of accepting or rejecting the order based on the compatibility of the deciduous tooth with buyer's 212 selected metallic jewelry object.

In a sixth step of the method, manufacturer 250 processes the deciduous tooth and sets the processed tooth in a metallic jewelry object to create the jewelry article that was selected by buyer 212.

In a seventh step of the method, manufacturer 250 sends or otherwise delivers 256 the jewelry article containing the processed deciduous tooth to buyer 212. The delivery 256 may be made by any convenient means, such as by postal mail 260.

One embodiment includes an additional step of certifying that the processed tooth contained in the jewelry article sent to buyer 212 is the tooth that buyer 212 sent to manufacturer 250. The certification may be delivered 256 with the processed jewelry article. Alternatively, it may be provided electronically over the Internet.

The solicitation delivery 224 may be an emailed correspondence, or it may be a brochure or catalog. The solicitation 224 may include an Internet 100 URL address for manufacturer 250.

Buyer 212 may be a member of organization 220, or the parent or adult caretaker of a child 214 member of organization 220, such as a student of school 222, congregation member of a religious organization 224, scout or other member of a social organization 226, or patient of dental clinic 228. In one embodiment, child 214 is under 13 years of age.

In the fourth step identified above, manufacturer 250 delivers 252 a special shipping container to buyer 212 for containing the deciduous tooth. This is necessary since, unlike any other fund raising process, the present invention requires the buyer to ship an article to the manufacturer of the final product. It is also necessary since, unlike any other fund raising process, the present invention requires shipment of a biological material. These are significant obstacles to the process.

The shipping container provided to solve this problem is an assembly of multiple components. A small first container is partially fluid filled. The container must be well constructed with a secure lid to prevent leaking during transport 252 and transport 254. The solution provides moisture to prevent dehydration of the tooth. The fluid should contain disinfecting properties to protect employees at the manufacturing facility. Thus, a preferred fluid is a liquid chemical germicide that will disinfect the teeth and also keep them hydrated. A 10% formalin solution may be used for this purpose. Another example of an acceptable solution is glutaraldehyde, 5.25% sodium hypochlorite.

The first container is labeled with a unique identifier generated for identifying the buyer. The first container is then enclosed in a second container. The second container is designed to further protect the first container from impact and crushing forces. In a preferred embodiment, the second container is also made of an absorbent material that may absorb liquid leaked from the first container. Alternatively, an absorbent packing material can be placed between the first and second containers. Each container should be marked with the biohazard symbol.

In a further step of the invention, the first and second containers are located inside a third container, being a shipping box or envelope. This container may have the shipping address of the manufacturer 250. This third container is preferably stamped with postage paid for return shipping to manufacturer 250. In a further step, the nesting first, second, and third containers are placed in a fourth container, addressed to the buyer 212.

Special handling instructions are included in the fourth container. Preferably, the fourth container is a child-proof container. All components, as well as the complete assembly of the four nesting containers, must be compliant with government regulations for shipping biological materials. As it can be seen from the above, besides the novelty of the invention, there are several regulatory obstacles that render the invention non-obvious to perform.

In various embodiments of the invention, the jewelry article can be a keepsake item associated with the tooth fairy, or a jewelry frame wearable for personal adornment. The wearable article may be a jewelry frame of religious significance, or of sentimental value, or even of fashion value.

In various embodiments of the invention, the jewelry article can be a baby shoe charm, wherein the processed deciduous tooth is mounted inside the baby shoe over an insole portion of the shoe. The processed deciduous tooth may extend slightly above a topline portion of the shoe.

In one embodiment of the invention, the step of processing the tooth includes the further steps of substantially disinfecting the tooth; filling a pulp chamber of the tooth with a solidifying bonding agent; and shaping an exterior surface of the tooth for complementary fit within the metallic jewelry object.

In one embodiment of the invention, the step of processing the tooth includes the further steps of substantially disinfecting the tooth wherein the deciduous tooth has an occlusal side having an irregular surface formed thereon, substantially filling the irregular surface with a solidifying bonding agent and shaping an exterior surface of the tooth for complementary fit within the metallic jewelry object.

In one embodiment of the invention, the step of processing the tooth includes the further steps of shaping an exterior surface of the tooth to create a pair of substantially parallel sides.

In one embodiment of the invention, the step of processing the tooth includes the further steps of shaping an exterior surface of the tooth to create two pairs of substantially parallel sides.

It will be appreciated that these processing steps may be combined as deemed desirable and efficient.

While this invention has been described in connection with a preferred embodiment, it is not intended to limit the scope of the invention to the particular form set forth, but, on the contrary, is intended to cover such alternatives, modifications and equivalents as may be included within the spirit and scope of the invention as defined by the appended claims.

The invention claimed is:

1. A method of raising funds for an organization, comprising:
    distributing a solicitation to a buyer, or to an organization for delivery to the buyer;
    the buyer being a relative or custodian of a child;
    the solicitation comprising an offer to sell a jewelry article;
    the jewelry article comprising a processed exfoliated deciduous tooth of the child set in a metallic jewelry object;
    receiving payment for the jewelry article from the buyer;
    issuing a payment to the organization;
    receiving the exfoliated deciduous tooth from the buyer;
    shaping an exterior surface of the tooth to form a pair of substantially parallel sides for complementary fit in the jewelry article; and,
    sending the jewelry article with the shaped exfoliated deciduous tooth to the buyer.

2. The method of claim 1, further comprising:
    sending a first container to the buyer; and,
    the first container having a label for marking the identity of the child.

3. The method of claim 2, further comprising:
    receiving the first container from the buyer, the first container including an exfoliated deciduous tooth of the child.

4. The method of claim 1, further comprising:
    shaping the exfoliated deciduous tooth to have a square shaped perimeter.

5. The method of claim 1, further comprising:
    receiving an order for the jewelry article electronically over the Internet.

6. The method of claim 1, the step of receiving payment further comprising:
    receiving a payment for the jewelry article by electronic charge authorization made over the Internet.

7. The method of claim 1, the step of issuing a payment to the organization further comprising:
    issuing a payment to the organization by electronic charge authorization made over the Internet.

8. The method of claim 1, the solicitation further comprising:
    instructions to place the container under the pillow of the child.

9. The method of claim 1, the solicitation further comprising:
    instructions to write the name of the child on the first container label.

10. The method of claim 8, the solicitation further comprising:
    an instruction to write a note or letter to the Tooth Fairy.

11. The method of claim 1, further comprising:
    the organization being a not-for-profit entity.

12. The method of claim 1, further comprising:
the organization being a school or charitable organization.
13. The method of claim 1, further comprising:
the organization being a religious entity.
14. The method of claim 1, further comprising:
the organization being a social entity.
15. The method of claim 1, further comprising:
the organization being a dental clinic.
16. The method of claim 1, further comprising:
the solicitation being an emailed correspondence.
17. The method of claim 1, further comprising:
the solicitation being an order form, brochure, or catalog.
18. The method of claim 1, further comprising:
the solicitation including an Internet url address for a manufacturer of the jewelry article.
19. The method of claim 1, further comprising:
the buyer being a member of the organization.
20. The method of claim 1, further comprising:
the buyer being the parent of a member of the organization.
21. The method of claim 1, further comprising:
the child being under 13 years of age.
22. The method of claim 1, further comprising:
the child being a member of the organization.
23. The method of claim 1, further comprising:
the child being a student of the organization.
24. The method of claim 1, further comprising:
substantially filling a pulp chamber of the exfoliated deciduous tooth with a solidifying bonding agent.
25. The method of claim 1, further comprising:
setting a facial side of the exfoliated deciduous tooth in the jewelry article as a displayed side.

* * * * *